US011478426B2

(12) United States Patent
Lai et al.

(10) Patent No.: US 11,478,426 B2
(45) Date of Patent: Oct. 25, 2022

(54) ABUSE DETERRENT IMMEDIATE RELEASE CAPSULE DOSAGE FORMS

(71) Applicant: SpecGX LLC, Webster Groves, MO (US)

(72) Inventors: Tsz Chung Lai, Webster Groves, MO (US); Rebecca Sue Walker, Webster Groves, MO (US); Chirag Patel, Webster Groves, MO (US); Jaehan Park, Webster Groves, MO (US)

(73) Assignee: SpecGX LLC, Webster Groves, MO (US)

(*) Notice: Subject to any disclaimer, the term of this patent is extended or adjusted under 35 U.S.C. 154(b) by 0 days.

(21) Appl. No.: 16/574,699

(22) Filed: Sep. 18, 2019

(65) Prior Publication Data

US 2020/0093749 A1   Mar. 26, 2020

Related U.S. Application Data

(63) Continuation of application No. 62/736,020, filed on Sep. 25, 2018.

(51) Int. Cl.
| | |
|---|---|
| *A61K 9/46* | (2006.01) |
| *A61K 9/20* | (2006.01) |
| *A61K 9/48* | (2006.01) |
| *A61K 31/485* | (2006.01) |

(52) U.S. Cl.
CPC .......... *A61K 9/2077* (2013.01); *A61K 9/2027* (2013.01); *A61K 9/2054* (2013.01); *A61K 9/4866* (2013.01); *A61K 31/485* (2013.01)

(58) Field of Classification Search
None
See application file for complete search history.

(56) References Cited

U.S. PATENT DOCUMENTS

| | | | |
|---|---|---|---|
| 2,211,485 | A | 8/1940 | Zimmermann |
| 3,891,756 | A | 6/1975 | Kasugai et al. |
| 3,980,766 | A | 9/1976 | Shaw et al. |
| 4,070,494 | A | 1/1978 | Hoffmeister et al. |
| 4,678,661 | A | 7/1987 | Gergely et al. |
| 4,956,182 | A | 9/1990 | Bequette et al. |
| 5,096,714 | A | 3/1992 | Kuhrts |
| 5,486,364 | A | 1/1996 | King et al. |
| 6,071,539 | A | 6/2000 | Robinson et al. |
| 6,200,604 | B1 | 3/2001 | Pather et al. |
| 6,264,981 | B1 | 7/2001 | Zhang et al. |
| 6,309,668 | B1 | 10/2001 | Bastin et al. |
| 6,340,471 | B1 | 1/2002 | Kershman et al. |
| 6,541,025 | B1 | 4/2003 | Kershman et al. |
| 6,713,089 | B1 | 3/2004 | Bertelsen et al. |
| 7,201,920 | B2 | 4/2007 | Kumar et al. |
| 7,510,726 | B2 | 3/2009 | Kumar et al. |
| 7,658,944 | B2 | 2/2010 | Holm et al. |
| 7,776,314 | B2 | 8/2010 | Bartholomaus et al. |
| 7,955,619 | B2 | 6/2011 | Shah et al. |
| 8,075,872 | B2 | 12/2011 | Arkenau-Maric et al. |
| 8,114,383 | B2 | 2/2012 | Bartholomaus et al. |
| 8,114,384 | B2 | 2/2012 | Arkenau et al. |
| 9,301,918 | B2 | 4/2016 | Raman et al. |
| 9,993,422 | B2 | 6/2018 | Raman et al. |
| 2003/0049272 | A1* | 3/2003 | Joshi .................... A61K 9/0056 424/195.18 |
| 2003/0049311 | A1 | 3/2003 | McAllister et al. |
| 2003/0068375 | A1 | 4/2003 | Wright et al. |
| 2004/0005359 | A1 | 1/2004 | Cheng et al. |
| 2005/0165038 | A1 | 7/2005 | Gordon |
| 2005/0236741 | A1 | 10/2005 | Arkenau et al. |
| 2005/0245557 | A1 | 11/2005 | Schoenhard et al. |
| 2006/0002860 | A1 | 1/2006 | Bartholomaus et al. |
| 2006/0193782 | A1 | 8/2006 | Bartholomaus et al. |
| 2007/0004795 | A1 | 1/2007 | Sesha |
| 2007/0048228 | A1 | 3/2007 | Arkenau-Maric et al. |
| 2007/0166234 | A1 | 7/2007 | Kumar et al. |
| 2007/0183980 | A1 | 8/2007 | Arkenau-Maric et al. |
| 2008/0102121 | A1 | 5/2008 | Devane et al. |
| 2008/0166405 | A1 | 7/2008 | Mehta |
| 2008/0247959 | A1 | 10/2008 | Bartholomaus et al. |
| 2008/0248113 | A1 | 10/2008 | Bartholomaus et al. |
| 2008/0280975 | A1 | 11/2008 | Badul |
| 2008/0311187 | A1 | 12/2008 | Ashworth et al. |
| 2008/0311205 | A1 | 12/2008 | Habib et al. |
| 2009/0081290 | A1 | 3/2009 | McKenna et al. |
| 2009/0098200 | A1 | 4/2009 | Temtsin Krayz et al. |

(Continued)

FOREIGN PATENT DOCUMENTS

| | | |
|---|---|---|
| AU | 2013206525 A1 | 8/2013 |
| EP | 2123274 A1 | 11/2009 |

(Continued)

OTHER PUBLICATIONS

Beer et al., "Impact of slow-release oral morphine on drug abusing habits in Austria", Neuropsychiatrie, Dustri Verlag, Deisenhofen, DE, vol. 24, No. 2; Jan. 1, 2010; pp. 108-117.

Bhatt et al., "Pharmaceutical Engineering: Mixing", 2007, pp. 1-24, <nsdl.niscair.res.in/jspui/bitstream/123456789/751/1/Revised%20mixing.pdf>.

Born et al., Chapter 11, "Xanthan", 2002, pp. 259-269, downloaded from the internet at URL <http://www.wiley-vch.do/books/biopoly/pdf_v05/bpol5011_259_269.pdf>.

International Search Report and Written Opinion from related International Patent Application No. PCT/US2013/037056, dated Jun. 24, 2013; 9 pgs.

International Search Report and Written Opinion from related International Patent Application No. PCT/US2013/037046, dated Jul. 3, 2013; 12 pgs.

International Search Report and Written Opinion from related International Patent Application No. PCT/US2013/050005, dated Aug. 19, 2013; 11 pgs.

(Continued)

*Primary Examiner* — David J Blanchard
*Assistant Examiner* — Daniel F Coughlin

(57) ABSTRACT

Capsule dosage forms that provide immediate release of active ingredients and have abuse deterrent properties. In particular, the dosage forms comprise at least one pharmaceutically active ingredient, a combination of hydrophilic gelling polymers, at least one organic acid, and at least one disintegrant.

16 Claims, No Drawings

(56) References Cited

U.S. PATENT DOCUMENTS

| | | |
|---|---|---|
| 2009/0124650 A1 | 5/2009 | Ahdieh |
| 2009/0175937 A1 | 7/2009 | Rahmouni et al. |
| 2009/0196922 A1 | 8/2009 | Guerrero et al. |
| 2009/0205534 A1 | 8/2009 | Sunnucks |
| 2009/0221621 A1 | 9/2009 | Sathyan et al. |
| 2009/0232887 A1 | 9/2009 | Odidi et al. |
| 2009/0317355 A1 | 12/2009 | Roth et al. |
| 2010/0092553 A1 | 4/2010 | Guimberteau et al. |
| 2010/0151028 A1 | 6/2010 | Ashworth et al. |
| 2010/0166858 A1 | 7/2010 | Mehta et al. |
| 2010/0168148 A1 | 7/2010 | Wright et al. |
| 2010/0203130 A1 | 8/2010 | Tygesen et al. |
| 2010/0204259 A1 | 8/2010 | Tygesen et al. |
| 2010/0260833 A1 | 10/2010 | Bartholomaus et al. |
| 2011/0020451 A1 | 1/2011 | Bartholomaus et al. |
| 2011/0038930 A1 | 2/2011 | Barnscheid et al. |
| 2011/0054038 A1 | 3/2011 | Glozman |
| 2011/0117196 A1 | 5/2011 | Gordon |
| 2011/0136921 A1 | 6/2011 | Dumbre et al. |
| 2011/0165248 A1 | 7/2011 | Machonis |
| 2011/0268666 A1 | 11/2011 | Friedman et al. |
| 2012/0028937 A1 | 2/2012 | Tsuzuki et al. |
| 2012/0135075 A1 | 5/2012 | Mohammad |
| 2012/0136021 A1 | 5/2012 | Barnscheid et al. |
| 2012/0214777 A1 | 8/2012 | Crowley et al. |
| 2012/0321674 A1 | 12/2012 | Vachon et al. |
| 2012/0321716 A1 | 12/2012 | Vachon et al. |
| 2013/0171212 A1 | 7/2013 | Leskovar et al. |
| 2013/0171256 A1 | 7/2013 | Hamed |
| 2013/0209560 A1 | 8/2013 | Hamed et al. |
| 2013/0266660 A1 | 10/2013 | Hamed |
| 2013/0280176 A1 | 10/2013 | Diezi et al. |
| 2013/0280177 A1 | 10/2013 | Raman et al. |
| 2014/0010873 A1 | 1/2014 | Tygesen et al. |
| 2014/0017310 A1 | 1/2014 | Gower et al. |
| 2015/0313846 A1 | 11/2015 | Guimberteau et al. |
| 2016/0000703 A1 | 1/2016 | Micka et al. |
| 2016/0022590 A1 | 1/2016 | Odidi |
| 2017/0281615 A1* | 10/2017 | Gaik ............... A61K 9/1635 |

FOREIGN PATENT DOCUMENTS

| | | |
|---|---|---|
| EP | 2161021 A1 | 3/2010 |
| JP | 62-089616 | 4/1987 |
| JP | 2011105615 A | 6/2011 |
| MX | 2015012060 A | 1/2016 |
| WO | 02/19987 A1 | 3/2002 |
| WO | 03/032954 A1 | 4/2003 |
| WO | 03/033031 A1 | 4/2003 |
| WO | 2006/002836 A1 | 1/2006 |
| WO | 2007/009806 A2 | 1/2007 |
| WO | 2007/117605 A2 | 10/2007 |
| WO | 2008/011595 A2 | 1/2008 |
| WO | 2008/033523 A1 | 3/2008 |
| WO | 2008/039737 A2 | 4/2008 |
| WO | 2008/086804 A2 | 7/2008 |
| WO | 2008/128191 A2 | 10/2008 |
| WO | 2009/092601 A1 | 7/2009 |
| WO | 2011/066980 A2 | 6/2011 |
| WO | 2011/079074 A1 | 6/2011 |
| WO | 2011/143118 A2 | 11/2011 |
| WO | 2012/028318 A1 | 3/2012 |
| WO | 2012/112952 A1 | 8/2012 |
| WO | 2013/077851 A1 | 5/2013 |
| WO | 2013/158810 A1 | 10/2013 |
| WO | 2013/158814 A1 | 10/2013 |
| WO | 2014/011830 A1 | 1/2014 |
| WO | 2014/047731 A1 | 4/2014 |
| WO | 2014/152296 A1 | 9/2014 |
| WO | 2016/004170 A1 | 1/2016 |
| WO | 2018137018 A1 | 8/2018 |

OTHER PUBLICATIONS

International Search Report and Written Opinion from related International Patent Application No. PCT/US2015/038774, dated Oct. 6, 2015; 8 pgs.

Koo et al., "Investigation into Stability of Poly(Vinyl Alcohol)-Based Opadry II Films", AAPS PharmSciTech, Jun. 2011, pp. 746-754, vol. 12, No. 2.

Opadry II Application Data, The Effect of Coating Process Conditions and Coating Formula Type on the Quantity and Location of Water in Film Coated Tablets, Colorcon, 2009, 5 pgs.

Patil et al., "Hot-Melt Extrusion: from Theory to Application in Pharmaceutical Formulation", AAPS PharmSciTech, Feb. 2016, pp. 20-42, vol. 17, No. 1.

Polyox Water-Soluble Resins brochure, 2002, 24 pgs., downloaded from the internet from URL <http://msdssearch.dow.com/PublishedLiteratureDOWCOM/dh_0046/0901b80380046565.pdf?filepath=polyox/pdfs/noreg/326-00002.pdf&fromPage=GetDoc>.

Shah et al., "Polyox (Polyethylene Oxide) Multifunctional Polymer in Novel Drug Delivery System", Int. J. Pharm. Sci. Drug Res., 2014, pp. 95-101, vol. 6, No. 2.

Supplementary European Search Report from related European Application No. 15815497.1, dated Nov. 7, 2017, 7 pgs.

Usui et al., "Interactions in the Solid State I: Interactions of Sodium Bicarbonate and Tartaric Acid Under Compressed Conditions", Journal of Pharmaceutical Sciences, 1985, pp. 1293-1297, vol. 74, No. 12.

Alonso-Sande et al., "Glucomannan, a promising polysaccharide for biopharmaceutical purposes", European Journal of Pharmaceutics and Biopharmaceutics, 2009, pp. 453-462, vol. 72.

Bhowmik et al., "Controlled Release Drug Delivery Systems", The Pharma Innovation Journal, 2012, pp. 24-32, vol. 1, No. 10.

International Preliminary Report on Patentability dated Oct. 21, 2014 from related International Application No. PCT/US2013/037046; 7 pgs.

International Preliminary Report on Patentability dated Oct. 21, 2014 from related International Application No. PCT/US2013/037056; 6 pgs.

International Search Report and Written Opinion dated Jul. 10, 2014 from related International Application No. PCT/US2014/027176; 10 pgs.

Lubrizol Technical Data Sheet, Molecular Weight of Carbopol and Pemulen Polymers, TDS-222, Oct. 15, 2007; 3 pgs.

Rowe, Polyethylene Oxide, Handbook of Pharmaceutical Excipients, Sixth edition, Pharmaceutical Press, 2009, pp. 522-524.

Rowe, Xanthan Gum, Handbook of Pharmaceutical Excipients, Sixth edition, Pharmaceutical Press, 2009, pp. 782-785.

Extended European Search Report for Application No. 19867805.4, dated Jun. 3, 2022, 7 Pages.

\* cited by examiner

ABUSE DETERRENT IMMEDIATE RELEASE CAPSULE DOSAGE FORMS

CROSS-REFERENCE TO RELATED APPLICATIONS

This application claims the priority of U.S. Provisional Application Ser. No. 62/736,020, filed Sep. 25, 2018, the disclosure of which is hereby incorporated by reference in its entirety.

FIELD

The present disclosure generally relates to pharmaceutical compositions that provide immediate release of active ingredients and have abuse deterrent properties.

BACKGROUND

Abuse of prescription drugs (particularly opioids) has become a serious societal problem. Such abuse places an enormous economic burden on society due to increased health care, work place, and criminal justice costs. Several routes of administration are commonly attempted by abusers. For example, the oral solid dosage form may be crushed or pulverized into a powder and administered intranasally (i.e., snorted) or dissolved in a suitable solvent (e.g., water) and administered parenterally (i.e., injected intravenously).

Attempts have been made to diminish the abuse of opioid solid dosage forms. One approach has been to include in the dosage form an opioid antagonist that is not orally active but will substantially block the analgesic effects of the opioid if one attempts to dissolve the opioid and administer it parenterally. Another approach has been to include gel-forming high molecular weight polymers that confer plasticity to the dosage form rendering them difficult to crush and pulverize into a powder. These high molecular weight polymers, however, retard the release of the active ingredient from the dosage forms, making them unsuitable for immediate release formulations.

Thus, there is a need for oral solid dosage forms that provide immediate release of the active ingredient yet are resistant to abuse.

SUMMARY

One aspect of the present disclosure encompasses abuse deterrent capsule dosage forms comprising granular fill encapsulated by a capsule shell. The granular fill comprises at least one active pharmaceutical ingredient (API) susceptible to abuse or a pharmaceutically acceptable salt thereof; a combination of hydrophilic gelling polymers comprising at least one natural gum, at least one cellulose ether, and at least one polyalkylene oxide; at least one organic acid; and at least one disintegrant, wherein the granular fill is devoid of a metal carbonate or a metal bicarbonate and the capsule shell has a wall thickness of less than about 0.5 mm.

The abuse deterrent capsule dosage form provides immediate release of the at least one API. For example, at least about 50% of the at least one API is released from the capsule dosage form within about 45 minutes when dissolution is measured using an USP-approved in vitro release procedure.

The at least one organic acid deters abuse of the dosage form by causing nasal irritation when the granular fill is inhaled. The combination of hydrophilic gelling polymers deters abuse of the dosage from by forming a viscous mixture or gel when the granular fill is mixed with about 2 mL to about 10 mL of an aqueous solvent.

In some embodiments, the at least one natural gum is glucomannan, xanthan gum, guar gum, gum arabic, karaya gum, gellan gum, dextran, welan gum, diutan gum, pullulan, or a combination thereof; the at least one cellulose ether is hydroxypropylcellulose, hydroxypropylmethylcellulose, sodium carboxymethylcellulose, methylcellulose, hydroxyethylcellulose, hydroxyethylmethylcellulose, methylhydroxyethylcellulose, or a combination thereof; and wherein the at least one polyalkylene oxide is a polyethylene oxide having an average molecular weight of less than 500,000, a polyethylene oxide having an average molecular weight of greater than 1,000,000, or a combination thereof. In certain embodiments, the combination of hydrophilic gelling polymers is present in an amount from about 10% to about 70% by weight of the granular fill.

In some embodiments, the at least one organic acid is adipic acid, ascorbic acid, benzoic acid, citric acid, fumaric acid, glutaric acid, lactic acid, lauric acid, malic acid, maleic acid, malonic acid, oxalic acid, phthalic acid, sorbic acid, succinic acid, tartaric acid, or a combination thereof, and the at least one organic acid is present in an amount from about 10% to about 60% by weight of the granular fill.

In various embodiments, the at least one disintegrant is crospovidone, croscarmellose sodium, sodium starch glycolate, microcrystalline cellulose, fumed silica, talc, alginate, clay, or a combination thereof, and the at least one disintegrant is present in an amount from about 2% to about 70% by weight of the granular fill.

In some embodiments, the at least one API is an opioid or a combination of an opioid and a non-opioid analgesic, and the opioid is oxycodone, oxymorphone, hydrocodone, hydromorphone, codeine, or morphine.

In certain embodiments, the capsule shell of the abuse deterrent capsule dosage form has a wall thickness of i less than about 0.4 mm, less than 0.3 mm, or less than 0.25 mm.

In some embodiments, the at least one API is oxycodone, oxymorphone, hydrocodone, hydromorphone, codeine, or morphine, the at least one natural gum is glucomannan, xanthan gum, or a combination thereof, the at least one cellulose ether is hydroxypropylmethylcellulose, sodium carboxymethylcellulose, or a combination thereof, the at least one polyalkylene oxide is a first polyethylene oxide having an average molecular weight of about 100,000, a second polyethylene oxide having an average molecular weight of about 4,000,000, or a combination thereof, the at least one organic acid is citric acid, tartaric acid, or a combination thereof, and the at least one disintegrant is crospovidone, fumed silica, talc, or a combination thereof.

In certain embodiments, the at least one natural gum is present in an amount from about 6% to about 35% (w/w) of the granular fill; the at least one cellulose ether is present in an amount from about 3% to about 25% (w/w) of the granular fill; the at least one polyalkylene oxide is present in an amount from about 20% to about 40% (w/w) of the granular fill when both the first and the second polyethylene oxide are present or the at least one polyalkylene oxide is present in an amount from about 0.5% to about 3% (w/w) of the granular fill when only the second polyethylene oxide is present; the at least one organic acid is present in an amount from about 10% to about 60% (w/w) of the granular fill; and the at least one disintegrant is present in an amount from about 2% to about 10% (w/w) of the granular fill with fumed silica is present or the at least one disintegrant is present in an amount from about 40% to about 70% (w/w) of the granular fill when crospovidone and talc are present.

In some embodiments, the abuse deterrent capsule dosage form further comprises at least one lubricant, at least one preservative, or a combination thereof, optionally wherein the at least one lubricant is magnesium stearate, polyethylene glycol, stearic acid, or a combination thereof, and the at least one preservative is butylated hydroxytoluene, alpha-tocopherol, ascorbyl palmitate, or a combination thereof.

Other aspects and features of the present disclosure are detailed below.

DETAILED DESCRIPTION

The present disclosure provides pharmaceutical compositions that provide rapid release of the active ingredients and have abuse deterrent properties. In particular, the pharmaceutical composition disclosed herein is a capsule dosage form comprising a granular fill encapsulated by a capsule shell, wherein the capsule shell has a wall thickness of less than about 0.5 mm. The granular fill comprises at least one active pharmaceutical ingredient (API) susceptible to abuse or a pharmaceutically acceptable salt thereof, a combination of hydrophilic gelling polymers, at least one organic acid, and at least one disintegrant, wherein the combination of hydrophilic gelling polymers comprises at least one natural gum, at least one cellulose ether, and at least one polyalkylene oxide. Notably, the granular fill is devoid of a metal carbonate or a metal bicarbonate. The various components of the capsule dosage form contribute to the abuse deterrent properties of the composition. For example, the at least one organic acid causes nasal irritation when the granular fill is inhaled, thereby deterring nasal inhalation. Also, the combination of hydrophilic gelling polymers forms a viscous mixture or gel when the granular fill is mixed with about 3 mL to about 15 mL, thereby deterring abuse by intravenous injection.

(I) Capsule Dosage Forms

One aspect of the present disclosure provides abuse deterrent capsule dosage forms that provide immediate release of the active pharmaceutical ingredients. The capsule dosage forms comprise a granular fill encapsulated by a capsule shell. Detailed below are the components and properties of the capsule dosage forms.

(a) Granular Fill

The granular fill of the capsule dosage forms comprise at least one active pharmaceutical ingredient (API) or a pharmaceutically acceptable salt thereof, a combination of hydrophilic gelling polymers, at least one organic acid, and at least one disintegrant. The granular fill is a dry, free flowing blend of powders or small granules/particles. The granular fill can be prepared as described below in section (II).

(i) Hydrophilic Gelling Polymers

Among the constituents of the granular fill is a combination of hydrophilic gelling polymers. The term "hydrophilic gelling polymer" refers to a polymer with affinity for water such that it readily absorbs water or an aqueous solution and/or swells when in contact with water or an aqueous solution to form a viscous mixture or gel. The combination of hydrophilic gelling polymers included in the granular fill of the capsule comprises at least one natural gum, at least one cellulose ether, and at least one polyalkylene oxide.

The combination of hydrophilic gelling polymers is generally present in an amount from about 10% to about 70% by weight of the granular fill. In some embodiments, the total amount of the hydrophilic gelling polymers may range from about 15% to about 65%. For examples, the total amount of the hydrophilic gelling polymers may range from about 15% to about 30%, from about 30% to about 50%, or from about 50% to about 65% by weight of the granular fill.

Natural Gums.

Natural gums are non-cellulose polysaccharides derived from botanical sources, seaweeds, or produced via bacterial fermentation. Natural gums are water-soluble and/or water-swellable polymers that are capable of forming highly viscous gels even at low concentrations. Non-limiting examples of plant-derived natural gums include glucomannan, albizia gum, aloe mucilage, beta-glucan, chicle gum, dammar gum, fenugreek gum, guar gum, gum arabic (also called acacia gum), gum copal, gum ghatti, gum tragacanth, hakea gum, *Hibiscus rosasinensis* gum, honey locust gum, hupu gum, karaya gum, khaya gum, *Lepidium sativum* gum, locust bean gum, mastic gum, *Mimosa scabrella* gum, *Mimosa pudica* gum, okra gum, psyllium seed husks (also called ispaghula husk), spruce gum, *Sterculia foetida* gum, tamarind gum, tara gum, and derivatives of any of the foregoing. Examples of natural gums derived from seaweeds include, without limit, alginate or alginic acid, fucoidan, and laminarin derived from brown seaweeds, and agar and carrageenans derived from red seaweeds. Non-limiting examples of natural gums produced by bacterial fermentation include xanthan gum, gellan gum, dextran, welan gum, diutan gum, pullulan, and derivatives thereof. In certain embodiments, the natural gum is chosen from glucomannan, xanthan gum, guar gum, gum arabic, karaya gum, gellan gum, dextran, welan gum, diutan gum, pullulan, or combinations thereof. In certain embodiments, the at least one natural gum is glucomannan, xanthan gum, guar gum, gum arabic, karaya gum, gellan gum, dextran, welan gum, diutan gum, pullulan, or a combination thereof. In specific embodiments, the natural gum(s) may be glucomannan, xanthan gum, or a combination thereof.

In general, the natural gum has a high molecular weight and forms a viscous mixture or gel upon contact with water or an aqueous solution. The molecular weight distribution of natural gums can range from about 200,000 to about 20,000,000. In some embodiments, the natural gum may be a glucomannan and/or xanthan gum having an average molecular weight of greater than about 500,000, greater than about 1,000,000, greater than about 2,000,000, or greater than about 4,000,000.

The amount of the natural gum(s) present in the granular fill of the capsule can and will vary depending upon the identity of the natural gum(a) and the identity and amounts of other components present in the granular fill. In general, the amount of the natural gum(s) in the formulation may range from about 6% to about 35% by weight of the granular fill. In various embodiments, the amount of the natural gum(s) may range from about 8% to about 30% or from about 10% to about 25% by weight of the granular fill.

Cellulose Ethers.

Cellulose ethers are cellulose derivatives in which the hydrogen atoms of hydroxyl groups are replaced with alkyl groups. The degree of substitution can and will vary. Non-limiting examples of suitable cellulose ethers include hydroxypropylcellulose (HPC), hydroxypropylmethylcellulose (HPMC), carboxymethylcellulose (CMC) (e.g., sodium carboxymethylcellulose), methylcellulose, hydroxyethylcellulose, hydroxyethylmethylcellulose, methylhydroxyethylcellulose, and the like. In some embodiments, the at least one cellulose ether may be hydroxypropylcellulose, hydroxypropylmethylcellulose, sodium carboxymethylcellulose, or combinations thereof. In specific embodiments, the at least one cellulose ether may be hydroxypropylcellulose, sodium carboxymethylcellulose, or combinations thereof.

The average molecular weight of the cellulose ether may range from about 20,000 to about 1,500,000. In various embodiments, the weight average molecular weight of the cellulose ether may be about 30,000, about 100,000, about 250,000, about 850,000, or about 1,150,000.

The amount of the cellulose ether(s) present in the granular fill can and will vary depending upon the identity of the cellular ether(s) and the identity and amounts of other components present in the granular fill. In general, the amount of the cellulose ether(s) may range from about 3% to about 25% by weight of the granular fill. In various embodiments, the amount of cellulose ether(s) may range from about 4% to about 20% or from about 5% to about 15% by weight of the granular fill.

Polyalkylene Oxides.

Suitable polyalkylene oxides include polyethylene oxide (PEO), polypropylene oxide (PPO), derivatives thereof, copolymers thereof, or combinations thereof. In particular embodiments, the at least one polyalkylene oxide may be a polyethylene oxide, wherein the average molecular weight of the polyethylene oxide may be 100,000, 200,000, 300,000, 600,000, 900,000, 1,000,000, 2,000,000, 4,000,000, 5,000,000, or 7,000,000. In some instances the least one polyalkylene oxide may be a combination of polyethylene oxides of different molecular weights. For example, a polyethylene oxide having an average molecular weight of less than 500,000, a polyethylene oxide having an average molecular weight of greater than 1,000,000. In particular embodiments, the at least one polyalkylene oxide comprises one polyethylene oxide. For example, the one polyethylene oxide may have an average molecular weight of greater than 1,000,000 (e.g., about 4,000,000). In other embodiments, the at least one polyalkylene oxide comprises two polyethylene oxides having different molecular weights. For example, a polyethylene oxide having an average molecular weight of about 100,000, and a polyethylene oxide having an average molecular weight of about 4,000,000.

The amount of the polyalkylene oxide(s) present in the granular fill can and will vary depending upon the identity of the polyalkylene oxide(s) and the identity and amounts of other components present in the formulation. In general, the amount of the polyalkylene oxide(s) may range from about 0.5% to about 40% by weight of the granular fill. In embodiments comprising one polyethylene oxide having an average molecular weight of greater than 1,000,000, the amount of polyethylene oxide may range from about 0.5% to about 3% by weight of the granular fill. In embodiments comprising two polyethylene oxides having different molecular weights, the amount of the polyethylene oxides may range from about 20% to about 40% or from about 25% to about 35% by weight of the granular fil.

(ii) Organic Acids

The granular fill of the capsule dosage form also comprises at least one organic acid. The organic acid(s) may contribute to the abuse deterrent properties of the formulation by functioning as a nasal irritant, when present at high levels. In certain embodiments, the organic acid(s) may provide antioxidant activity, and as such, may prevent degradation of the API(s).

Non-limiting examples of suitable organic acids include adipic acid, ascorbic acid, benzoic acid, citric acid, fumaric acid, glutaric acid, lactic acid, lauric acid, malic acid, maleic acid, malonic acid, oxalic acid, phthalic acid, sorbic acid, succinic acid, tartaric acid, or combinations thereof. In specific embodiments, the at least one organic acid may be citric acid, tartaric acid, or a combination thereof.

The amount of the organic acid(s) present in the granular fill can and will vary depending upon the identity of the organic acid(s) and the identity and amount of the other components of the formulation. In general, the amount of the organic acid(s) may range from about 10% to about 60% by weight of the granular fill. In various embodiments, the amount of the organic acid(s) may range from about 15% to about 55% or from about 20% to about 50% by weight of the granular fill.

(iii) Disintegrants

The granular fill also comprises at least one disintegrant. In general, disintegrants facilitate dissolution of the formulation. Non-limiting examples of suitable disintegrants include crospovidone, croscarmellose sodium, sodium carboxymethylcellulose, carboxymethylcellulose calcium, sodium starch glycolate, cellulose, microcrystalline cellulose, methylcellulose, fumed silica (e.g., AEROSIL®), talc, silicon dioxide (also called colloidal silicone dioxide), alginates, clays, and combinations of any of the foregoing. In specific embodiments, the at least one disintegrant may be crospovidone, fumed silica, talc, or a combination thereof.

The amount of the disintegrant(s) present in the granular fill can and will vary depending upon the identity of the disintegrant(s) and the identity and amounts of the other components of the formulation. In general, the amount of the disintegrant(s) may range from about 2% to about 70% by weight of the granular fill. In embodiments in which the disintegrant is fumed silica, the amount of disintegrant may range from about 2% to about 10%. In embodiments in which the disintegrant comprises crospovidone, the amount of disintegrant may range from about 40% to about 70% by weight of the granular fill.

(iv) Additional Excipients

Lubricants.

In some embodiments, the granular fill of the capsule dosage form disclosed herein may also comprise a lubricant. Non-limiting examples of suitable lubricants include metal stearates (e.g., magnesium stearate, calcium stearate, zinc stearate) polyethylene glycols, poloxamers, colloidal silicon dioxide, glyceryl behenate, light mineral oil, hydrogenated vegetable oils, magnesium lauryl sulfate, magnesium trisilicate, polyoxyethylene monostearate, sodium stearoyl fumarate, sodium stearyl fumarate, sodium benzoate, sodium lauryl sulfate, stearic acid, sterotex, talc, and combinations thereof. In specific embodiments, the lubricant may be a metal stearate. In one iteration, the lubricant may be magnesium stearate, polyethylene glycol, stearic acid, or a combination thereof.

The amount of lubricant present in the particulate fill can and will vary depending upon the identity of the lubricant and the identity and amount of other components in the formulation. In embodiments in which a lubricant is present, the amount of lubricant generally ranges from about 0.1% to about 2% by weight of the granular fill. In various embodiments, the amount of lubricant may range from about 0.1% to about 0.3%, from about 0.3 to about 1%, or from about 1% to about 3% by weight of the granular fill. In specific embodiments, the amount of lubricant may range from about 0.3% to about 1% by weight of the granular fill.

Preservatives.

In additional embodiments, the granular fill of the capsule dosage form disclosed herein may also comprise at least one preservative. Non limiting examples of suitable preservatives include antioxidants (such as, e.g., tocopherol or a derivative thereof (e.g., alpha-tocopherol), ascorbic acid or a derivative thereof (e.g., ascorbyl palmitate, ascorbyl oleate, ascorbyl stearate), butylated hydroxyanisole, butylated hydroxytoluene, citric acid, dihydroguaretic acid, potassium ascorbate, potassium sorbate, propylgallate, sodium bisulfate, sodium isoascorbate, sodium metabisulfate, sorbic acid, 4-chloro-2,6-ditertiarybutylphenol, and so forth), antimicrobials (such as, e.g., benzyl alcohol, cetylpryidine chloride, glycerine, parabens, propylene glycol, potassium sorbate, sodium benzoate, sorbic acid, sodium propionate, and the like), and combinations thereof. In specific embodiments, the preservative may be butylated hydroxytoluene, alpha-tocopherol, ascorbyl palmitate, or a combination thereof.

The amount of preservative present in the granular fill can and will vary depending upon the identity of the preservative and the identity and amount of the API(s). In embodiments in which a preservative is present, the amount of preservative may range from about 0.005% to about 3% by weight of the granular fill. In various embodiments, the amount of preservative may range from about 0.005% to about 0.03%, from about 0.03 to about 0.1%, from about 0.1% to about 0.3%, from about 0.3% to about 1.0%, or from about 1% to about 3% by weight of the granular fill. In specific embodiments, the amount of preservative may range from about 0.01% to about 0.04% by weight of the granular fill.

(v) API

The granular fill of the capsule dosage form disclosed herein comprises at least one API or a pharmaceutically acceptable salt thereof. Suitable APIs include, without limit, opioid analgesic agents (e.g., adulmine, alfentanil, allocryptopine, allylprodine, alphaprodine, anileridine, aporphine, benzylmorphine, berberine, bicuculine, bicucine, bezitramide, buprenorphine, bulbocaprine, butorphanol, clonitazene, codeine, desomorphine, dextromoramide, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, fentanyl, heroin, hydrocodone, hydromorphone, hydroxypethidine, isomethadone, ketobemidone, levorphanol, levophenacylmorphan, lofentanil, meperidine, meptazinol, metazocine, methadone, metopon, morphine, myrophine, narceine, nicomorphine, norlevorphanol, normethadone, nalorphine, nalbuphine, nalmefene, normorphine, norpipanone, opium, oxycodone, oxymorphone, papaveretum, pentazocine, phenadoxone, phenomorphan, phenazocine, phenoperidine, piminodine, piritramide, propheptazine, promedol, properidine, propoxyphene, sufentanil, tapentadol, tilidine, and tramadol); opioid antagonists (e.g., naloxone, naltrexone, alvimopan, cyprodime, diprenorphine, gemazocine, 5'-guanidinonaltrindole, levallorphan, methylnaltrexone, naldemedine, nalmexone, nalorphine, naloxazone, naloxol, naloxonazine, 6β-naltrexol-d4, naltriben, naltrindole, norbinaltorphimine, oxilorphan, quadazocine, and samidorphan); non-opioid analgesic agents (e.g., acetylsalicylic acid, acetaminophen, paracetamol, ibuprofen, ketoprofen, indomethacin, diflunisol, naproxen, ketorolac, dichlophenac, tolmetin, sulindac, phenacetin, piroxicam, and mefamanic acid); anti-inflammatory agents (e.g., glucocorticoids such as alclometasone, fluocinonide, methylprednisolone, triamcinolone and dexamethasone; non-steroidal anti-inflammatory agents such as celecoxib, deracoxib, ketoprofen, lumiracoxib, meloxicam, parecoxib, rofecoxib, and valdecoxib); antitussive agents (e.g., dextromethorphan, codeine, hydrocodone, caramiphen, carbetapentane, and dextromethorphan); antipyretic agents (e.g., acetylsalicylic acid and acetaminophen); antibiotic agents (e.g., aminoglycosides such as, amikacin, gentamicin, kanamycin, neomycin, netilmicin, streptomycin, and tobramycin; carbecephem such as loracarbef; carbapenems such as certapenem, imipenem, and meropenem; cephalosporins such as cefadroxil cefazolin, cephalexin, cefaclor, cefamandole, cephalexin, cefoxitin, cefprozil, cefuroxime, cefixime, cefdinir, cefditoren, cefoperazone, cefotaxime, cefpodoxime, ceftazidime, ceftibuten, ceftizoxime, and ceftriaxone; macrolides such as azithromycin, clarithromycin, dirithromycin, erythromycin, and troleandomycin; monobactam; penicillins such as amoxicillin, ampicillin, carbenicillin, cloxacillin, dicloxacillin, nafcillin, oxacillin, penicillin G, penicillin V, piperacillin, and ticarcillin; polypeptides such as bacitracin, colistin, and polymyxin B; quinolones such as ciprofloxacin, enoxacin, gatifloxacin, levofloxacin, lomefloxacin, moxifloxacin, norfloxacin, ofloxacin, and trovafloxacin; sulfonamides such as mafenide, sulfacetamide, sulfamethizole, sulfasalazine, sulfisoxazole, and trimethoprim-sulfamethoxazole; tetracyclines such as demeclocycline, doxycycline, minocycline, and oxytetracycline); antimicrobial agents (e.g., ketoconazole, amoxicillin, cephalexin, miconazole, econazole, acyclovir, and nelfinavir); antiviral agents (e.g., acyclovir, gangciclovir, oseltamivir, and relenza); steroids (e.g., estradiol, testosterone, cortisol, aldosterone, prednisone, and cortisone); amphetamine stimulant agents (e.g., amphetamine and amphetamine-like drugs); non-amphetamine stimulant agents (e.g., methylphenidate, nicotine, and caffeine); laxative agents (e.g., bisacodyl, casanthranol, senna, and castor oil); anti-nausea agents (e.g., dolasetron, granisetron, ondansetron, tropisetron, meclizine, and cyclizine); anorexic agents (e.g., fenfluramine, dexfenfluramine, mazindol, phentermine, and aminorex); antihistaminic agents (e.g., phencarol, cetirizine, cinnarizine, ethamidindole, azatadine, brompheniramine, hydroxyzine, and chlorpheniramine); antiasthmatic agents (e.g., zileuton, montelukast, omalizumab, fluticasone, and zafirlukast); antidiuretic agents (e.g., desmopressin, vasopressin, and lypressin); antimigraine agents (e.g., naratriptan, frovatriptan, eletriptan, dihydroergotamine, zolmitriptan, almotriptan, and sumatriptan); antispasmodic agents (e.g., dicyclomine, hyoscyamine, and peppermint oil); antidiabetic agents (e.g., methformin, acarbose, miglitol, pioglitazone, rosiglitazone, nateglinide, repaglinide, mitiglinide, saxagliptin, sitagliptine, vildagliptin, acetohexamide, chlorpropamide, gliclazide, glimepiride, glipizide, glyburide, tolazamide, and tolbutamide); respiratory agents (e.g., albuterol, ephedrine, metaproterenol, and terbutaline); sympathomimetic agents (e.g., pseudoephedrine, phenylephrine, phenylpropanolamine, epinephrine, norepinephrine, dopamine, and ephedrine); H2 blocking agents (e.g., cimetidine, famotidine, nizatidine, and ranitidine); antihyperlipidemic agents (e.g., clofibrate, cholestyramine, colestipol, fluvastatin, atorvastatin, genfibrozil, lovastatin, niacin, pravastatin, fenofibrate, colesevelam, and simvastatin); antihypercholesterol agents (e.g., lovastatin, simvastatin, pravastatin, fluvastatin, atorvastatin, cholestyramine, colestipol, colesevelam, nicotinic acid, gemfibrozil, and ezetimibe); cardiotonic agents (e.g., digitalis, ubidecarenone, and dopamine); vasodilating agents (e.g., nitroglycerin, captopril, dihydralazine, diltiazem, and isosorbide dinitrate); vasoconstricting agents (e.g., dihydroergotoxine and dihydroergotamine); anticoagulants (e.g., warfarin, heparin, and Factor Xa inhibitors); sedative agents (e.g., amobarbital, pentobarbital, secobarbital, clomethiazole, diphenhydramine hydrochloride, and alprazolam); hypnotic agents (e.g., zaleplon, zolpidem, eszopiclone, zopiclone, chloral hydrate, and clomethiazole); anticonvulsant agents (e.g., lamitrogene, oxycarbamezine, phenytoin, mephenytoin, ethosuximide, methsuccimide, carbamazepine, valproic acid, gabapentin, topiramate, felbamate, and phenobarbital); muscle relaxing agents (e.g., baclofen, carisoprodol, chlorzoxazone, cyclobenzaprine, dantrolene sodium, metaxalone, orphenadrine, pancuronium bromide, and tizanidine); antipsychotic agents (e.g., phenothiazine, chlorpromazine, fluphenazine, perphenazine, prochlorperazine, thioridazine, trifluoperazine, haloperidol, droperidol, pimozide, clozapine, olanzapine, risperidone, quetiapine, ziprasidone, melperone, and paliperidone); antianxiolitic agents (e.g., lorazepam, alprazolam, clonazepam, diazepam, buspirone, meprobamate, and flunitrazepam); antihyperactive agents (e.g., methylphenidate, amphetamine, and dextroamphetamine); antihypertensive agents (e.g., alpha-methyldopa, chlortalidone, reserpine, syrosingopine, rescinnamine, prazosin, phentolamine, felodipine, propanolol, pindolol, labetalol, clonidine, captopril, enalapril, and lisonopril); anti-neoplasia agents (e.g., taxol, actinomycin, bleomycin A2, mitomycin C, daunorubicin, doxorubicin, epirubicin, idarubicin, and mitoxantrone); soporific agents (e.g., zolpidem tartrate, eszopiclone, ramelteon, and zaleplon); tranquilizer agents (e.g., alprazolam, clonazepam, diazepam, flunitrazepam, lorazepam, triazolam, chlorpromazine, fluphenazine, haloperidol, loxapine succinate, perphenazine, prochlorperazine, thiothixene, and trifluoperazine); decongestant agents (e.g., ephedrine, phenylephrine, naphazoline, and tetrahydrozoline); beta blockers (e.g., levobunolol, pindolol, timolol maleate, bisoprolol, carvedilol, and butoxamine); alpha blockers (e.g., doxazosin, prazosin, phenoxybenzamine, phentolamine, tamsulosin, alfuzosin, and terazosin); non-steroidal hormones (e.g., corticotropin, vasopressin, oxytocin, insulin, oxendolone, thyroid hormone, and adrenal hormone); erectile disfunction improvement agents; herbal agents (e.g., glycyrrhiza, aloe, garlic, nigella sativa, rauwolfia, St John's wort, and valerian); enzymes (e.g., lipase, protease, amylase, lactase, lysozyme, and urokinase); humoral agents (e.g., prostaglandins, natural and synthetic, for example, PGE1, PGE2alpha, PGF2alpha, and the PGE1 analog misoprostol); psychic energizers (e.g., 3-(2-aminopropy)indole and 3-(2-aminobutyl)indole); nutritional agents; essential fatty acids; non-essential fatty acids; vitamins; minerals; and combinations thereof.

Any of the above-mentioned APIs may be incorporated in the dosage form described herein in any suitable form, such as, for example, as a pharmaceutically acceptable salt, uncharged or charged molecule, molecular complex, solvate or hydrate, prodrug, and, if relevant, isomer, enantiomer, racemic mixture, and/or mixtures thereof. Furthermore, the API may be in any of its crystalline, semi-crystalline, amorphous, or polymorphous forms.

In one embodiment, the API in the granular fill of the capsule dosage form may have a potential for abuse. For example, the API may be an opioid analgesic agent, a stimulant agent, a sedative agent, a hypnotic agent, an antianxiolitic agent, or a muscle relaxing agent.

In another embodiment, the API in the granular fill of the capsule dosage form may be a combination of an opioid analgesic and a non-opioid analgesic. Suitable opioid and non-opioid analgesics are listed above.

In a further embodiment, the API in the granular fill of the capsule dosage form may be a combination of an opioid analgesic and an opioid antagonist, examples of which are listed above.

In a specific embodiment, the API in the granular fill of the capsule dosage form may be an opioid analgesic. Exemplary opioid analgesics include oxycodone, oxymorphone, hydrocodone, hydromorphone, codeine, and morphine. In one specific embodiment, the API may be oxycodone hydrochloride. In another specific embodiment, the API may be oxymorphone hydrochloride.

The amount of API in the granular fill of the capsule dosage form can and will vary depending upon the identity of the active agent and the desired dosage level. In embodiments in which the API is an opioid analgesic, the amount of opioid in the dosage form may range from about 2 mg to about 160 mg. In various embodiments, the amount of opioid in the dosage form may range from about 2 mg to about 10 mg, from about 10 mg to about 40 mg, from about 40 mg to about 80 mg, or from about 80 mg to about 160 mg. In certain embodiments, the amount of opioid in the dosage form may be about 5 mg, 7.5 mg, 10 mg, 12.5 mg, 15 mg, 17.5 mg, 20 mg, 22.5 mg, 25 mg, 27.5 mg, 30 mg, 32.5 mg, 35 mg, 37.5 mg, 40 mg, 45 mg, 50 mg, 60 mg, 70 mg, 80 mg, 100 mg, 120 mg, 140 mg, or 160 mg.

In embodiments in which the opioid is oxycodone hydrochloride, the total amount of oxycodone hydrochloride present in the dosage form may range from about 2 mg to about 80 mg. In certain embodiments, the amount of oxycodone hydrochloride in the dosage form may range from about 2 mg to about 10 mg, from about 10 mg to about 30 mg, or from about 30 mg to about 80 mg. In specific embodiments, the amount of oxycodone hydrochloride present in the dosage form may be about 5 mg, about 10 mg, about 15 mg, about 20 mg, about 30 mg, about 40 mg, about 60 mg, or about 80 mg.

In embodiments in which the opioid is oxymorphone hydrochloride, the total amount of oxymorphone hydrochloride present in the dosage form may range from about 2 mg to about 80 mg. In certain embodiments, the amount of oxymorphone hydrochloride present in the dosage form may range from about 2 mg to about 10 mg, from about 10 mg to about 30 mg, or from about 30 mg to about 80 mg. In specific embodiments, the amount of oxymorphone hydrochloride present in the dosage form may be about 5 mg, about 10 mg, about 20 mg, about 30 mg, or about 40 mg.

(vi) Optional Additional Excipients

In various embodiments, the granular fill of the capsule dosage form disclosed herein may further comprise at least one additional pharmaceutically acceptable excipient. Non-limiting examples of suitable excipients include binders, fillers, diluents, chelating agents, flavoring agents, coloring agents, taste masking agents, and combinations thereof.

In a further embodiment, the optional excipient may be a binder. Suitable binders include, but are not limited to, starches, pregelatinized starches, gelatin, polyvinylpyrolidone, cellulose, methylcellulose, sodium carboxymethylcellulose, ethylcellulose, polyacrylamides, polyvinylalcohols, C12-C18 fatty acid alcohols, polyethylene glycols, polyols, saccharides, oligosaccharides, polypeptides, peptides, and combinations thereof.

In another embodiment, the optional excipient may be a filler. Suitable fillers include, without limit, calcium carbonate, calcium phosphate, calcium sulfate, calcium silicate, magnesium carbonate, magnesium oxide, sodium chloride, starch, modified starches, cellulose, microcrystalline cellulose, sucrose, lactose, dextrose, mannitol, sorbitol, talc, and combinations thereof.

In another embodiment, the optional excipient may be a diluent. Non-limiting examples of diluents suitable for use include pharmaceutically acceptable saccharides such as sucrose, dextrose, lactose, microcrystalline cellulose, cellulose, cellulose derivatives, starches, fructose, xylitol, and sorbitol, polyhydric alcohols, pre-manufactured direct compression diluents, and mixtures of any of the foregoing.

In an alternate embodiment, the optional excipient may be a chelating agent. Non-limiting examples of suitable chelating agents include ethylenediamine tetracetic acid (EDTA) and its salts, N-(hydroxy-ethyl)ethylenediaminetriacetic acid, nitrilotriacetic acid (NIA), ethylene-bis(oxyethylene-nitrilo)tetraacetic acid, 1,4,7,10-tetraazacyclodo-decane-N,N',N'',N'''-tetraacetic acid, 1,4,7,10-tetraaza-cyclododecane-N,N',N''-triacetic acid, 1,4,7-tris(carboxymethyl)-10-(2'-hydroxypropyl)-1,4,7,10-tetraazocyclodecane, 1,4,7-triazacyclonane-N,N',N''-triacetic acid, 1,4,8,11-tetraazacyclotetra-decane-N,N',N'',N'''-tetraacetic acid; diethylenetriamine-pentaacetic acid (DTPA), ethylenedicysteine, bis(aminoethanethiol)carboxylic acid, triethylenetetraamine-hexaacetic acid, and 1,2-diaminocyclohexane-N,N,N',N'-tetraacetic acid.

In a further embodiment, the optional excipient may be a flavoring agent. Flavoring agents may be chosen from synthetic flavor oils and flavoring aromatics and/or natural oils, extracts from plants, leaves, flowers, fruits, and combinations thereof.

In still another embodiment, the optional excipient may be a coloring agent. Suitable color additives include food, drug and cosmetic colors (FD&C), drug and cosmetic colors (D&C), or external drug and cosmetic colors (Ext. D&C).

In yet another embodiment, the optional excipient may be a taste-masking agent. Taste-masking materials include, but are not limited to, cellulose ethers, polyethylene glycols, polyvinyl alcohol, polyvinyl alcohol and polyethylene glycol copolymers, monoglycerides or triglycerides, acrylic polymers, mixtures of acrylic polymers with cellulose ethers, cellulose acetate phthalate, and combinations thereof.

The amount of the one or more additional excipients in the dosage form can and will vary depending upon the identity of the excipient and the identities and amounts of the other components of the granular fill of the capsule dosage forms.

(vii) Specific Embodiments

In specific embodiments, the granular fill of the capsule dosage form comprises from about 6% to about 35% (w/w) of glucomannan and xanthan gum, from about 3% to about 25% (w/w) of hydroxypropylmethylcellulose and sodium carboxymethyl cellulose; about 0.5% to about 3% (w/w) of one polyethylene oxide having an average molecular weight of about 4,000,000, or about 20% to about 40% (w/w) of two polyethylene oxides, a first with an average molecular weight of about 100,000 and a second with an average molecular weight of about 4,000,000; about 10% to about 60% (w/w) of citric acid; about 2% to about 10% (w/w) of fumed silica, or about 40% to about 70% (w/w) of crospovidone and talc; and API chosen from oxycodone, oxymorphone, hydrocodone, hydromorphone, codeine, or morphine. The granular fill may further comprise a lubricant, such as magnesium stearate, and a preservative, such as butylated hydroxytoluene.

(b) Shell of the Capsule

The granular fill, described above in section (I)(a), is encapsulated by a capsule shell. In general the capsule shell is a hard shell comprising two pieces, a body piece and a cap piece. The capsule shell may be constructed of different materials. In some embodiments, the capsule shell may be a gelatin shell, i.e., comprised of gelatin, which is manufactured from collagen derived from animal bones or skin. In other embodiments, the capsule shell may be a vegetable shell, i.e., comprised of polymers (e.g., celluloses, starches) of plant origin. For example, vegetable capsules may be comprised of a cellulose derivative, e.g., hydroxypropylmethylcellulose (also called hypomellose). Alternatively, vegetable capsules may be comprised of pullulan, which is polysaccharide polymer produced from tapioca starch.

In general, the capsule shell has an average wall thickness of less than about 0.5 mm. In various embodiments, the average thickness of the shell wall may be less than about 0.45 mm, less than about 0.40 mm, less than about 0.35 mm, less than about 0.30 mm, less than about 0.25 mm, less than 0.20 mm, or less than about 0.15 mm. In certain embodiments, the capsule shell has a wall thickness that ranges from about 0.020 to about 0.022 mm.

The overall length and diameter of the capsule shell can and will vary depending upon the composition of the granular fill and the dosage level of the API. Those of skill in the art are familiar with standard sizes, which are usually designated by different numbers, with 5 being the smallest and 000 being the largest.

(c) In Vitro Release Properties

The capsule dosage form disclosed herein is formulated such that the API is released rapidly from the formulation. Thus, the dosage form is termed an immediate release pharmaceutical composition. As used herein, "immediate release" refers to an average release of at least 50% of the API within 45 minutes using a USP approved in vitro release test. Unlike many immediate release compositions, the dosage form disclosed herein comprises a blend of high molecular hydrophilic gelling polymers. The disclosed formulation, therefore, also comprises disintegrant(s) to facilitate dissolution of the formulation and rapid release of the API from the granular fill.

The in vitro dissolution of the API from the capsule dosage form disclosed herein may be measured using an approved USP procedure. For example, dissolution may be measured using an USP approved Type 2 paddle apparatus, with or without a sinker, at a paddle speed of 50 rpm or 100 rpm, and a constant temperature of 37±0.5° C. The dissolution test may be performed in the presence of 500 mL, 900 mL, or 1,000 mL of a suitable dissolution medium. Non-limiting examples of suitable dissolution media include water, phosphate buffer (pH 6.8), acetate buffer (pH 4.5), and 0.1N HCl.

The capsule dosage forms disclosed herein provide immediate release of the API. In some embodiments, the dosage form may have an average release of about 50%, 55%, 60%, 65%, 70%, 75%, 80%, 85%, 90%, 95%, or 99% of the API within 45 minutes in the dissolution solution.

(d) Abuse Deterrent Properties

The capsule dosage forms disclosed herein also have abuse deterrent features. The granular fill of the capsule comprises a relatively high concentration of at least one organic acid, which can cause nasal irritation. Thus, even though the capsule readily can be taken apart and the granular fill can be inhaled or snorted through the nose, the resultant nasal irritation, sneezing, runny nose, and postnasal drip may be unpleasant and aversive enough to deter such abuse.

The granular fill of the capsule dosage forms also comprises a combination of hydrophilic gelling polymers such that a viscous mixture or gel is formed when the granular fill is contacted with a small volume of a suitable solvent. The volume of solvent may range from about 2 mL to about 10 mL. For example, 2 mL, 2.5 mL, 3 mL, 3.5 mL, 4 mL, 4.5 mL, 5 mL, 6 mL, 7 mL, 8 mL, 9 mL, or 10 mL. In general, the suitable solvent may be an aqueous solvent. Suitable aqueous solvents include water, alcohols such as ethanol, acids such as acetic acid, fruit juice, and mixtures of any of the foregoing. The temperature of the extraction may range from about 4° C. to about 100° C. In certain embodiments, the temperature of the extraction may be about room temperature (i.e., about 23-25° C.), about 30° C., about 60° C., or about 90° C. The duration of the extraction may range from about 5 minutes to about 3 hours. In some embodiments, the duration of the extraction may be about 30 minutes or about 60 minutes. The viscosity of the resultant mixture or gel prevents the mixture or gel from being drawn through an injection syringe needle. Consequently, the capsule dosage forms disclosed herein are resistant to abuse by intravenous injection.

(II) Processes for Preparing Capsule Dosage Forms

Another aspect of the disclosure encompasses processes for preparing the capsule dosage forms disclosed herein. The processes comprise forming the granular fill and encapsulating the granular fill in capsule shells.

(a) Forming the Granular Fill

The first step of the process comprises forming the granular fill, the components of which are described above in section (I)(a). The individual components may be milled, ground, crushed, and/or sieved to form a powder or dry mixture comprising substantially uniformly sized particles or granules. The components may be combined in any order or may be premixed in various combinations before being combined together. For example, all the components may be mixed or blended to uniformly distribute the API within the fill mixture and then a lubricant may be added, followed by further mixing. The mixing may comprise roller mixing, drum mixing, shear mixing, dry blending, chopping, milling, roller milling, granulating, dry granulating (e.g., slugging or roller compacting), wet granulating (e.g., fluid bed granulating, high shear granulating), and other mixing techniques known in the art.

In some embodiments, the granular fill may be a blend of powders that was prepared by mixing the dry components. In other embodiments, the granular fill may be prepared by mixing/blending the components (including a lubricant), wet-granulating the mixture, drying the granulated mixture, and optionally sieving the dried granulate. In further embodiments, the granular fill may be prepared by mixing or blending the components to form a mixture, roller compacting the mixture, mixing a lubricant with the roller compacted mixture, and optionally sieving the mixture.

The granular fill is a dry free-flowing powder/granulate. It is not prepared by injection molding, thermos-molding, extrusion, heat extrusion, thermoforming, compression, or tabletting techniques.

(b) Encapsulating the Granular Fill

The process further comprises encapsulating the granular fill by filling capsule shells with the granular fill. Suitable capsule shells are described above in section (I)(b). The capsule shells may be filled using manual capsule filling machines, semi-automatic capsule filling machines, automatic capsule filling machines, fully automatic capsule filling machines, or industrial capsule filling machines. After the capsules are filled they may be polished using capsule polishing machines. Persons skilled in the art are familiar with means for filling and polishing capsules.

Definitions

When introducing components of the embodiments described herein, the articles "a", "an", "the" and "said" are intended to mean that there are one or more of the elements. The terms "comprising", "including" and "having" are intended to be inclusive and mean that there may be additional components other than the listed components.

If the components described herein have asymmetric centers, all chiral, diastereomeric, racemic forms and all geometric isomeric forms of a structure are intended, unless the specific stereochemistry or isomeric form is specifically indicated.

As used herein, "abuse deterrent" refers to any property or feature of a pharmaceutical composition that lessens the potential for abuse of the active ingredient(s) in the composition.

The terms "gum" or "natural gum" refer to water-soluble and/or water-swellable polysaccharides derived from natural sources, or structurally modified derivatives thereof, which are capable of forming highly viscous gels even at low concentrations.

The term "hydrophilic gelling polymer" refers to a polymer with affinity for water such that it readily absorbs water or an aqueous solution and/or swells when in contact with water or an aqueous solution to form a viscous mixture or gel.

As used herein, "immediate release" refers to an average release of at least 50% of the API within 45 minutes using a USP approved in vitro release procedure.

Having described the invention in detail, it will be apparent that modifications and variations are possible without departing from the scope of the invention defined in the appended claims.

EXAMPLES

The following examples are included to illustrate, but not to limit the claimed pharmaceutical compositions and processes for making.

Example 1: Preparation of Capsule Formulations

The composition of the capsule dosage forms 1-3 are listed in Table 1. Typical batch size was 30 g. All the ingredients except butylated hydroxytoluene (BHT) were manually sieved through a US Std 30 Mesh screen to remove any lumps. BHT was ground using a mortar and pestle, and then sieved through a US Std 60 Mesh screen. The required amounts of API and all excipients except magnesium stearate were weighed individually, placed in a plastic bag, and mixed manually for about 1.5 minutes. Magnesium stearate was then weighed and added to the bag, and the contents were mixed for additional 1 minute. Gelatin capsules (cap thickness=0.0081 in and body thickness=0.0082 in) were filled by weighing the required amount of blend and filling the capsules manually.

TABLE 1

Compositions of Capsule Formulations

| Ingredient | Capsule 1 mg | Capsule 1 w/w (%) | Capsule 2 mg | Capsule 2 w/w (%) | Capsule 3 mg | Capsule 3 w/w (%) |
|---|---|---|---|---|---|---|
| Oxycodone HCl | 15.91 | 3.53 | 15.91 | 7.49 | 15.91 | 4.60 |
| PEG 3350 | 7.05 | 1.56 | 7.05 | 3.32 | 7.05 | 2.04 |
| Polyox N10 LEO (100K) | 0 | 0 | 0 | 0 | 103.40 | 29.89 |
| BHT | 0.060 | 0.013 | 0.060 | 0.028 | 0.060 | 0.017 |
| Citric acid, anhydrous | 100.00 | 22.19 | 100.00 | 47.04 | 100.00 | 28.90 |
| Polyox WSR 301 LEO (4M) | 4.25 | 0.94 | 4.25 | 2.00 | 4.25 | 1.23 |
| Glucomannan | 40.00 | 8.88 | 40.00 | 18.82 | 40.00 | 11.56 |
| CMC-Na | 10.00 | 2.22 | 10.00 | 4.70 | 20.00 | 5.78 |
| HPMC K100M CR | 15.00 | 3.33 | 15.00 | 7.06 | 30.00 | 8.67 |
| Xanthan gum | 10.60 | 2.35 | 10.60 | 4.99 | 10.60 | 3.06 |
| Crospovidone | 200.00 | 44.39 | 0 | 0 | 0 | 0 |
| Talc | 45.93 | 10.19 | 0 | 0 | 0 | 0 |
| Aerosil | 0 | 0 | 7.97 | 3.75 | 12.96 | 3.75 |
| MgS | 1.75 | 0.39 | 1.75 | 0.82 | 1.75 | 0.51 |
| Total | 450.55 | 100.00 | 212.59 | 100.00 | 345.98 | 100.00 |

Example 2: Dissolution Analysis of Capsule Formulations

The in vitro release of oxycodone hydrochloride was determined using as USP approved process with sinkers for capsules. The dissolution parameters were: USP Apparatus Type 2 (paddles without sinkers), 50 rpm, 500 mL water, and at 37°±0.5° C. The amount of oxycodone HCl in the dissolution fluid was determined at regular intervals. The dissolution data are presented in Table 2. All formulations exhibited fast release of the active ingredient and drug release was found to be affected by the effervescent system in the formulation.

TABLE 2

In Vitro Dissolution of Oxycodone form Capsules in Water

| Time (mon) | % oxycodone dissolved Capsule 1 | Capsule 2 | Capsule 3 |
|---|---|---|---|
| 5 | 12% | 0% | 6% |
| 10 | 24% | 8% | 9% |
| 15 | 33% | 16% | 32% |
| 20 | 40% | 31% | 39% |
| 30 | 51% | 53% | 47% |
| 45 | 62% | 66% | 56% |

Example 3: Abuse Deterrence Tests—Syringeability with Aqueous Solvent

Contents from capsule formulations 1-3 were tested to determine how much liquid can be drawn through a cigarette filter and a needle (27 gauge) into a syringe. The less liquid that is drawn out, the better deterrence provided by the formulation against abuse by IV administration.

In one test, contents from each formulation were mixed (no stirring, lightly tapped to mix contents) with 2.5 mL or 5 mL of water for 5 and 30 minutes at room temperature. At the end of the each time period, the supernatant liquid was drawn out through a cigarette filter into a syringe. The amount of liquid in syringe was determined by weighing the syringe before and after drawing out the liquid. The results are shown in Table 3. The results demonstrated that a solution suitable for IV injection could not be easily prepared from any of the capsule dosage forms in every testing condition.

TABLE 3

Syringe ability Test Results in Water

| Capsule | Time (min) | Volume (mL) | N | Initial Wt of Powder (g) | Tare Wt of Syringe (g) | Gross Wt of Syringe (g) | Net Wt Syringed (mg) | Volume Syringed (mL) |
|---|---|---|---|---|---|---|---|---|
| 1 | 5 | 2.5 | 1 | 453.0 | 8.7731 | 8.7476 | −0.025 | 0 |
|   |   |   | 2 | 451.5 | 8.7850 | 8.7910 | 0.006 | 0 |
|   | 30 | 2.5 | 1 | 452.0 | 8.5802 | 8.5828 | 0.003 | 0 |
|   |   |   | 2 | 450.5 | 8.5705 | 8.5717 | 0.001 | 0 |
| 2 | 5 | 2.5 | 1 | 213.2 | 8.6990 | 8.6962 | −0.003 | 0 |
|   |   |   | 2 | 212.0 | 8.6771 | 8.6785 | 0.001 | 0 |
|   | 30 | 2.5 | 1 | 212.6 | 8.6845 | 8.6854 | 0.001 | 0 |
|   |   |   | 2 | 213.2 | 8.6242 | 8.6256 | 0.001 | 0 |
| 3 | 5 | 2.5 | 1 | 346.6 | 8.5656 | 8.5650 | −0.001 | 0 |
|   |   |   | 2 | 346.3 | 8.5350 | 8.5408 | 0.006 | 0 |
|   | 30 | 2.5 | 1 | 346.7 | 8.5879 | 8.5885 | 0.001 | 0 |
|   |   |   | 2 | 346.5 | 8.5792 | 8.5789 | 0.000 | 0 |

Example 4: Abuse Deterrence Tests—Slug Irritation Test of Organic Acid

The organic acid of the capsule contents was tested for potential nasal irritation using a slug irritation model. Slug species were exposed to various compounds for 15 min, and the amount of mucus produced as a result of mucosal irritation was measured. The results are presented in Table 4. The more mucus that is produced, the better deterrence provided by the formulation against abuse by nasal administration by causing more nasal irritation. Results indicate that the irritating effects of the organic acid may make the formulation resistant to abuse by intranasal administration.

TABLE 4

Slug Mucus production (% of Body Weight) After Administration of Irritants or Control Materials

| Dose (mg or %) | Mucus Production (% of Body Weight)[a] Benzalkonium Chloride (BAC) | NaHCO$_3$ | Tartaric Acid | NaHCO$_3$/ Tartaric Acid | Sodium Lauryl Sulfate |
|---|---|---|---|---|---|
| 0.3 mg | — | | | | 5.9 ± 2.0 (6) |
| 1.0 mg | — | 0.8 ± 1.9 (3) | | | 9.5 ± 2.1 (9) |
| 3.0 mg | — | 2.3 ± 1.1 (3) | 2.8 ± 2.4 (3) | | 13.4 ± 2.6 (3) |

TABLE 4-continued

Slug Mucus production (% of Body Weight) After Administration of Irritants or Control Materials

| Dose (mg or %) | Benzalkonium Chloride (BAC) | NaHCO$_3$ | Tartaric Acid | NaHCO$_3$/ Tartaric Acid | Sodium Lauryl Sulfate |
|---|---|---|---|---|---|
| 5.0 mg | — | 10.8 ± 1.0 (3) | 7.2 ± 0.7 (6) | | 9.8 ± 2.1 (6) |
| 10 mg | — | 2.9 ± 0.3 (3) | 10.0 ± 1.3 (3) | 5.6 ± 1.0 (3) | 16.6 ± 0.9 (3) |
| 15 mg | — | 18.2 ± 0.5 (3) | 33.6 ± 1.1 (6) | | 22.7 ± 4.5 (3) |
| 20 mg | — | 8.2 ± 2.5 (3) | 24.6 ± 2.8 (3) | 15.5 ± 1.5 (3) | 26.2 ± 3.8 (3) |
| 1% | 24.7 ± 2.1 (3) | | | | |

$^a$Data presented as mean ± standard error of the mean (n).

What is claimed is:

1. An abuse deterrent capsule dosage form comprising a granular fill encapsulated by a capsule shell, wherein the granular fill comprises at least one active pharmaceutical ingredient (API) susceptible to abuse or a pharmaceutically acceptable salt thereof, a combination of hydrophilic gelling polymers, at least one organic acid, and at least one disintegrant; wherein the combination of hydrophilic gelling polymers comprises at least one natural gum, at least one cellulose ether, and at least one polyalkylene oxide; the granular fill is devoid of a metal carbonate or a metal bicarbonate; the capsule shell has a wall thickness of less than 0.3 mm; the organic acid is present in an amount of about 20% to about 50% by weight of the granular fill; the at least one disintegrant is selected from crospovidone, talc, fumed silica, and combinations thereof, and the at least one disintegrant is present in an amount from about 2% to about 10% (w/w) of the granular fill when fumed silica is present, or the at least one disintegrant is present in an amount from about 40% to about 70% (w/w) of the granular fill when crospovidone and talc are present; and wherein the abuse deterrent capsule dosage form is an immediate-release dosage form.

2. The abuse deterrent capsule dosage form of claim 1, wherein the at least one natural gum is glucomannan, xanthan gum, guar gum, gum arabic, karaya gum, gellan gum, dextran, welan gum, diutan gum, pullulan, or a combination thereof.

3. The abuse deterrent capsule dosage form of claim 1, wherein the at least one cellulose ether is hydroxypropylcellulose, hydroxypropylmethylcellulose, sodium carboxymethylcellulose, methylcellulose, hydroxyethylcellulose, hydroxyethylmethylcellulose, methylhydroxyethylcellulose, or a combination thereof.

4. The abuse deterrent capsule dosage form of claim 1, wherein the at least one polyalkylene oxide is a polyethylene oxide having an average molecular weight of less than 500,000, a polyethylene oxide having an average molecular weight of greater than 1,000,000, or a combination thereof.

5. The abuse deterrent capsule dosage form of claim 1, wherein the combination of hydrophilic gelling polymers is present in an amount from about 10% to about 70% by weight of the granular fill.

6. The abuse deterrent capsule dosage form of claim 1, wherein the at least one organic acid is adipic acid, ascorbic acid, benzoic acid, citric acid, fumaric acid, glutaric acid, lactic acid, lauric acid, malic acid, maleic acid, malonic acid, oxalic acid, phthalic acid, sorbic acid, succinic acid, tartaric acid, or a combination thereof.

7. The abuse deterrent capsule dosage form of claim 1, wherein the at least one API is an opioid or a combination of an opioid and a non-opioid analgesic, and the opioid is oxycodone, oxymorphone, hydrocodone, hydromorphone, codeine, or morphine.

8. The abuse deterrent capsule dosage form of claim 1, wherein the wall thickness of the capsule shell is less than 0.15 mm.

9. The abuse deterrent capsule dosage form of claim 1, wherein at least about 50% of the at least one API is released from the capsule dosage form within about 45 minutes when dissolution is measured using an USP-approved in vitro release procedure.

10. The abuse deterrent capsule dosage form of claim 1, wherein the at least one organic acid deters abuse of the dosage form by causing nasal irritation when the granular fill is inhaled.

11. The abuse deterrent capsule dosage form of claim 1, wherein the combination of hydrophilic gelling polymers deters abuse of the dosage from by forming a viscous mixture or gel when the granular fill is mixed with about 2 mL to about 10 mL of an aqueous solvent.

12. The abuse deterrent capsule dosage form of claim 1, wherein the at least one API is oxycodone, oxymorphone, hydrocodone, hydromorphone, codeine, or morphine; the at least one natural gum is glucomannan, xanthan gum, or a combination thereof, the at least one cellulose ether is hydroxypropylmethylcellulose, sodium carboxymethylcellulose, or a combination thereof, the at least one polyalkylene oxide is a first polyethylene oxide having an average molecular weight of about 100,000, a second polyethylene oxide having an average molecular weight of about 4,000,000, or a combination thereof.

13. The abuse deterrent capsule dosage form of claim 12, wherein the at least one natural gum is present in an amount from about 6% to about 35% (w/w) of the granular fill; the at least one cellulose ether is present in an amount from about 3% to about 25% (w/w) of the granular fill; and the at least one polyalkylene oxide is present in an amount from about 20% to about 40% (w/w) of the granular fill when both the first and the second polyethylene oxide are present, or the at least one polyalkylene oxide is present in an amount from about 0.5% to about 3% (w/w) of the granular fill when only the second polyethylene oxide is present.

14. The abuse deterrent capsule dosage form of claim 13, further comprising at least one lubricant, at least one preservative, or a combination thereof.

15. The abuse deterrent capsule dosage form of claim 14, wherein the at least one lubricant is magnesium stearate, polyethylene glycol, stearic acid, or a combination thereof, and the at least one preservative is butylated hydroxytoluene, alpha-tocopherol, ascorbyl palmitate, or a combination thereof.

16. An abuse deterrent capsule dosage form comprising a granular fill encapsulated by a capsule shell, wherein the granular fill comprises:
- at least one active pharmaceutical ingredient (API) comprising oxycodone, oxymorphone, hydrocodone, hydromorphone, codeine, or morphine, or pharmaceutically acceptable salts thereof;
- a combination of hydrophilic gelling polymers comprising at least one natural gum present in an amount from about 6% to about 35% (w/w) of the granular fill, at least one cellulose ether present in an amount from about 3% to about 25% (w/w) of the granular fill, and at least one polyalkylene oxide comprising first polyethylene oxide having an average molecular weight of about 100,000, a second polyethylene oxide having an average molecular weight of about 4,000,000, wherein the at least one polyalkylene oxide is present in an amount from about 20% to about 40% (w/w) of the granular fill when both the first and the second polyethylene oxide are present, or the at least one polyalkylene oxide is present in an amount from about 0.5% to about 3% (w/w) of the granular fill when only the second polyethylene oxide is present;
- at least one organic acid present in an amount of about 20% to about 50% by weight of the granular fill;
- at least one disintegrant selected from crospovidone, fumed silica, talc, or a combination thereof, wherein the at least one disintegrant is present in an amount from about 2% to about 10% (w/w) of the granular fill with fumed silica is present, or the at least one disintegrant is present in an amount from about 40% to about 70% (w/w) of the granular fill when crospovidone and talc are present; and wherein the abuse deterrent capsule dosage form is an immediate-release dosage form, and wherein the capsule shell has a wall thickness that ranges from less than about 0.30 mm.

* * * * *